United States Patent
Ameri

(10) Patent No.: US 8,086,321 B2
(45) Date of Patent: Dec. 27, 2011

(54) SELECTIVELY CONNECTING THE TIP ELECTRODE DURING THERAPY FOR MRI SHIELDING

(75) Inventor: Masoud Ameri, Maple Plain, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 434 days.

(21) Appl. No.: 12/329,399

(22) Filed: Dec. 5, 2008

(65) Prior Publication Data

US 2009/0149909 A1  Jun. 11, 2009

Related U.S. Application Data

(60) Provisional application No. 60/992,990, filed on Dec. 6, 2007.

(51) Int. Cl.
*A61N 1/16* (2006.01)
(52) U.S. Cl. ............... 607/63; 607/2; 607/115
(58) Field of Classification Search ........... 607/2, 34, 607/36–37, 63, 115–117
See application file for complete search history.

(56) References Cited

U.S. PATENT DOCUMENTS

| | | | |
|---|---|---|---|
| 3,888,260 A | 6/1975 | Fischell | |
| 3,898,995 A | 8/1975 | Dresbach | |
| 4,091,818 A | 5/1978 | Brownlee et al. | |
| 4,379,459 A | 4/1983 | Stein | |
| 4,404,125 A | 9/1983 | Abolins et al. | |
| 4,516,579 A | 5/1985 | Irnich | |
| 4,611,127 A | 9/1986 | Ibrahim et al. | |
| 4,694,837 A | 9/1987 | Blakeley et al. | |
| 4,729,376 A | 3/1988 | DeCote, Jr. | |
| 4,751,110 A | 6/1988 | Gulla et al. | |
| 4,779,617 A | 10/1988 | Whigham | |
| 4,869,970 A | 9/1989 | Gulla et al. | |
| 4,934,366 A | 6/1990 | Truex et al. | |
| 5,038,785 A | 8/1991 | Blakeley et al. | |
| 5,075,039 A | 12/1991 | Goldberg | |

(Continued)

FOREIGN PATENT DOCUMENTS

EP  0530006  3/1993

(Continued)

OTHER PUBLICATIONS

Dempsey Mary F. et al., "Investigation of the Factors Responsible for Burns During MRI", *Journal of Magnetic Resonance Imaging* 2001;13:627-631.

(Continued)

*Primary Examiner* — Carl H Layno
*Assistant Examiner* — Paula J Stice
(74) *Attorney, Agent, or Firm* — Faegre & Benson LLP

(57) ABSTRACT

A medical device includes a pulse generator and an electrode configured to contact tissue in a body vessel. The medical device includes a lead that includes a lead connector. The lead connector connects a pulse generator with an electrode via a conductive path. An electrode switch is electrically connected between the lead conductor and the electrode. The electrode switch includes an open state preventing the conductive path between the lead and the electrode. The electrode switch includes a closed state establishing the conductive path between the lead and the electrode when a voltage is applied across the electrode switch that exceeds a threshold voltage. The electrode switch in the open state electrically shields the electrode from electromagnetic radiation and induced voltages during magnetic resonance imaging.

13 Claims, 8 Drawing Sheets

U.S. PATENT DOCUMENTS

| | | |
|---|---|---|
| 5,076,841 A | 12/1991 | Chen et al. |
| 5,120,578 A | 6/1992 | Chen et al. |
| 5,187,136 A | 2/1993 | Klobucar et al. |
| 5,188,117 A | 2/1993 | Steinhaus et al. |
| 5,197,468 A | 3/1993 | Proctor et al. |
| 5,217,010 A | 6/1993 | Tsilik et al. |
| 5,243,911 A | 9/1993 | Dow et al. |
| 5,279,225 A | 1/1994 | Dow et al. |
| 5,288,313 A | 2/1994 | Portner |
| 5,292,342 A | 3/1994 | Nelson et al. |
| 5,309,096 A | 5/1994 | Hoegnelid |
| 5,325,728 A | 7/1994 | Zimmerman et al. |
| 5,345,362 A | 9/1994 | Winkler |
| 5,391,188 A | 2/1995 | Nelson et al. |
| 5,406,444 A | 4/1995 | Selfried et al. |
| 5,424,642 A | 6/1995 | Ekwall |
| 5,438,990 A | 8/1995 | Wahlstrand et al. |
| 5,454,837 A | 10/1995 | Lindegren et al. |
| 5,470,345 A | 11/1995 | Hassler et al. |
| 5,523,578 A | 6/1996 | Herskovic |
| 5,527,348 A | 6/1996 | Winkler et al. |
| 5,529,578 A | 6/1996 | Struble |
| 5,545,187 A | 8/1996 | Bergstrom et al. |
| 5,562,714 A | 10/1996 | Grevious |
| 5,607,458 A | 3/1997 | Causey, III et al. |
| 5,609,622 A | 3/1997 | Soukup et al. |
| 5,618,208 A | 4/1997 | Crouse et al. |
| 5,620,476 A | 4/1997 | Truex et al. |
| 5,647,379 A | 7/1997 | Meltzer |
| 5,649,965 A | 7/1997 | Pons et al. |
| 5,650,759 A | 7/1997 | Hittman et al. |
| 5,662,694 A | 9/1997 | Lidman et al. |
| 5,683,434 A | 11/1997 | Archer |
| 5,687,735 A | 11/1997 | Forbes et al. |
| 5,694,952 A | 12/1997 | Lidman et al. |
| 5,697,958 A | 12/1997 | Paul et al. |
| 5,709,225 A | 1/1998 | Budgifvars et al. |
| 5,714,536 A | 2/1998 | Ziolo et al. |
| 5,722,998 A | 3/1998 | Prutchi et al. |
| 5,727,552 A | 3/1998 | Ryan |
| 5,735,884 A | 4/1998 | Thompson et al. |
| 5,749,910 A | 5/1998 | Brumwell et al. |
| 5,751,539 A | 5/1998 | Stevenson et al. |
| 5,759,197 A | 6/1998 | Sawchuk et al. |
| 5,764,052 A | 6/1998 | Renger |
| 5,766,227 A | 6/1998 | Nappholz et al. |
| 5,776,168 A | 7/1998 | Gunderson |
| 5,782,891 A | 7/1998 | Hassler et al. |
| 5,792,201 A | 8/1998 | Causey, III et al. |
| 5,800,496 A | 9/1998 | Swoyer et al. |
| 5,800,497 A | 9/1998 | Bakels et al. |
| 5,814,090 A | 9/1998 | Latterell et al. |
| 5,817,130 A | 10/1998 | Cox et al. |
| 5,827,997 A | 10/1998 | Chung et al. |
| 5,853,375 A | 12/1998 | Orr |
| 5,867,361 A | 2/1999 | Wolf et al. |
| 5,869,078 A | 2/1999 | Baudino |
| 5,870,272 A | 2/1999 | Seifried et al. |
| 5,871,509 A | 2/1999 | Noren |
| 5,877,630 A | 3/1999 | Kraz |
| 5,895,980 A | 4/1999 | Thompson |
| 5,905,627 A | 5/1999 | Brendel et al. |
| 5,959,829 A | 9/1999 | Stevenson et al. |
| 5,964,705 A | 10/1999 | Truwit et al. |
| 5,968,854 A | 10/1999 | Akopian et al. |
| 5,973,906 A | 10/1999 | Stevenson et al. |
| 5,978,204 A | 11/1999 | Stevenson |
| 5,978,710 A | 11/1999 | Prutchi et al. |
| 5,999,398 A | 12/1999 | Makl et al. |
| 6,008,980 A | 12/1999 | Stevenson et al. |
| 6,031,710 A | 2/2000 | Wolf et al. |
| 6,032,063 A | 2/2000 | Hoar et al. |
| 6,055,455 A | 4/2000 | O'Phelan et al. |
| 6,079,681 A | 6/2000 | Stern et al. |
| 6,101,417 A | 8/2000 | Vogel et al. |
| 6,147,301 A | 11/2000 | Bhatia |
| 6,161,046 A | 12/2000 | Maniglia et al. |
| 6,162,180 A | 12/2000 | Miesel et al. |
| 6,173,203 B1 | 1/2001 | Barkley et al. |
| 6,188,926 B1 | 2/2001 | Vock |
| 6,192,279 B1 | 2/2001 | Barreras, Sr. et al. |
| 6,198,968 B1 | 3/2001 | Prutchi et al. |
| 6,198,972 B1 | 3/2001 | Hartlaub et al. |
| 6,209,764 B1 | 4/2001 | Hartlaub et al. |
| 6,217,800 B1 | 4/2001 | Hayward |
| 6,235,038 B1 | 5/2001 | Hunter et al. |
| 6,245,464 B1 | 6/2001 | Spillman et al. |
| 6,246,902 B1 | 6/2001 | Naylor et al. |
| 6,249,701 B1 | 6/2001 | Rajasekhar et al. |
| 6,268,725 B1 | 7/2001 | Vernon et al. |
| 6,270,831 B2 | 8/2001 | Kumar et al. |
| 6,275,369 B1 | 8/2001 | Stevenson et al. |
| 6,288,344 B1 | 9/2001 | Youker et al. |
| 6,324,431 B1 | 11/2001 | Zarinetchi et al. |
| 6,358,281 B1 | 3/2002 | Berrang et al. |
| 6,365,076 B1 | 4/2002 | Bhatia |
| 6,381,494 B1 | 4/2002 | Gilkerson et al. |
| 6,421,555 B1 | 7/2002 | Nappholz |
| 6,424,234 B1 | 7/2002 | Stevenson |
| 6,446,512 B2 | 9/2002 | Zimmerman et al. |
| 6,452,564 B1 | 9/2002 | Schoen et al. |
| 6,456,481 B1 | 9/2002 | Stevenson |
| 6,459,935 B1 | 10/2002 | Piersma |
| 6,470,212 B1 | 10/2002 | Weijand et al. |
| 6,487,452 B2 | 11/2002 | Legay |
| 6,490,148 B1 | 12/2002 | Allen et al. |
| 6,496,714 B1 | 12/2002 | Weiss et al. |
| 6,503,964 B2 | 1/2003 | Smith et al. |
| 6,506,972 B1 | 1/2003 | Wang |
| 6,510,345 B1 | 1/2003 | Van Bentem |
| 6,512,666 B1 | 1/2003 | Duva |
| 6,522,920 B2 | 2/2003 | Silvian et al. |
| 6,526,321 B1 | 2/2003 | Spehr |
| 6,539,253 B2 | 3/2003 | Thompson et al. |
| 6,545,854 B2 | 4/2003 | Trinh et al. |
| 6,555,745 B1 | 4/2003 | Kruse et al. |
| 6,563,132 B1 | 5/2003 | Talroze et al. |
| 6,566,978 B2 | 5/2003 | Stevenson et al. |
| 6,567,259 B2 | 5/2003 | Stevenson et al. |
| 6,580,947 B1 | 6/2003 | Thompson |
| 6,584,351 B1 | 6/2003 | Ekwall |
| 6,595,756 B2 | 7/2003 | Gray et al. |
| 6,626,937 B1 | 9/2003 | Cox |
| 6,629,938 B1 | 10/2003 | Engvall |
| 6,631,290 B1 | 10/2003 | Guck et al. |
| 6,631,555 B1 | 10/2003 | Youker et al. |
| 6,640,137 B2 | 10/2003 | MacDonald |
| 6,643,903 B2 | 11/2003 | Stevenson et al. |
| 6,646,198 B2 | 11/2003 | Maciver et al. |
| 6,648,914 B2 | 11/2003 | Berrang et al. |
| 6,662,049 B1 | 12/2003 | Miller |
| 6,673,999 B1 | 1/2004 | Wang et al. |
| 6,711,440 B2 | 3/2004 | Deal et al. |
| 6,713,671 B1 | 3/2004 | Wang et al. |
| 6,718,203 B2 | 4/2004 | Weiner et al. |
| 6,718,207 B2 | 4/2004 | Connelly |
| 6,725,092 B2 | 4/2004 | MacDonald et al. |
| 6,731,979 B2 | 5/2004 | MacDonald |
| 6,795,730 B2 | 9/2004 | Connelly et al. |
| 6,901,292 B2 | 5/2005 | Hrdlicka et al. |
| 6,925,328 B2 | 8/2005 | Foster et al. |
| 6,937,906 B2 | 8/2005 | Terry et al. |
| 6,944,489 B2 * | 9/2005 | Zeijlemaker et al. .......... 600/373 |
| 6,963,779 B1 | 11/2005 | Shankar |
| 7,013,180 B2 | 3/2006 | Villaseca et al. |
| 7,050,855 B2 | 5/2006 | Zeijlemaker et al. |
| 7,076,283 B2 | 7/2006 | Cho et al. |
| 7,082,328 B2 | 7/2006 | Funke |
| 7,092,756 B2 | 8/2006 | Zhang et al. |
| 7,123,013 B2 | 10/2006 | Gray |
| 7,138,582 B2 | 11/2006 | Lessar et al. |
| 7,164,950 B2 | 1/2007 | Kroll et al. |
| 7,174,219 B2 | 2/2007 | Wahlstrand et al. |
| 7,174,220 B1 | 2/2007 | Chitre et al. |
| 7,212,863 B2 | 5/2007 | Strandberg |
| 7,231,251 B2 | 6/2007 | Yonce et al. |
| 7,242,981 B2 | 7/2007 | Ginggen |

| Patent No. | Date | Inventor(s) |
|---|---|---|
| 7,272,444 B2 * | 9/2007 | Peterson et al. ............. 607/30 |
| 7,369,898 B1 | 5/2008 | Kroll et al. |
| 7,388,378 B2 | 6/2008 | Gray et al. |
| 7,509,167 B2 | 3/2009 | Stessman |
| 7,561,915 B1 | 7/2009 | Cooke et al. |
| 7,835,803 B1 * | 11/2010 | Malinowski et al. ......... 607/122 |
| 2001/0002000 A1 | 5/2001 | Kumar et al. |
| 2001/0006263 A1 | 7/2001 | Hayward |
| 2001/0011175 A1 | 8/2001 | Hunter et al. |
| 2001/0018123 A1 | 8/2001 | Furumori et al. |
| 2001/0025139 A1 | 9/2001 | Pearlman |
| 2001/0037134 A1 | 11/2001 | Munshi |
| 2001/0050837 A1 | 12/2001 | Stevenson et al. |
| 2002/0019658 A1 | 2/2002 | Munshi |
| 2002/0026224 A1 | 2/2002 | Thompson et al. |
| 2002/0038135 A1 | 3/2002 | Connelly et al. |
| 2002/0050401 A1 | 5/2002 | Youker et al. |
| 2002/0072769 A1 | 6/2002 | Silvian et al. |
| 2002/0082648 A1 * | 6/2002 | Kramer et al. ............... 607/9 |
| 2002/0102835 A1 | 8/2002 | Stucchi et al. |
| 2002/0116028 A1 | 8/2002 | Greatbatch et al. |
| 2002/0116029 A1 | 8/2002 | Miller et al. |
| 2002/0116033 A1 | 8/2002 | Greatbatch et al. |
| 2002/0116034 A1 | 8/2002 | Miller et al. |
| 2002/0117314 A1 | 8/2002 | Maciver et al. |
| 2002/0128689 A1 | 9/2002 | Connelly et al. |
| 2002/0128691 A1 | 9/2002 | Connelly |
| 2002/0133086 A1 | 9/2002 | Connelly et al. |
| 2002/0133199 A1 | 9/2002 | MacDonald et al. |
| 2002/0133200 A1 | 9/2002 | Weiner et al. |
| 2002/0133201 A1 | 9/2002 | Connelly et al. |
| 2002/0133202 A1 | 9/2002 | Connelly et al. |
| 2002/0133208 A1 | 9/2002 | Connelly |
| 2002/0133211 A1 | 9/2002 | Weiner et al. |
| 2002/0133216 A1 | 9/2002 | Connelly et al. |
| 2002/0138102 A1 | 9/2002 | Weiner et al. |
| 2002/0138107 A1 | 9/2002 | Weiner et al. |
| 2002/0138108 A1 | 9/2002 | Weiner et al. |
| 2002/0138110 A1 | 9/2002 | Connelly et al. |
| 2002/0138112 A1 | 9/2002 | Connelly et al. |
| 2002/0138113 A1 | 9/2002 | Connelly et al. |
| 2002/0138124 A1 | 9/2002 | Helfer et al. |
| 2002/0143258 A1 | 10/2002 | Weiner et al. |
| 2002/0147388 A1 | 10/2002 | Mass et al. |
| 2002/0147470 A1 | 10/2002 | Weiner et al. |
| 2002/0162605 A1 | 11/2002 | Horton, Jr. et al. |
| 2002/0166618 A1 | 11/2002 | Wolf et al. |
| 2002/0175782 A1 | 11/2002 | Trinh et al. |
| 2002/0183796 A1 | 12/2002 | Connelly |
| 2002/0198569 A1 | 12/2002 | Foster et al. |
| 2003/0036774 A1 | 2/2003 | Maier et al. |
| 2003/0036776 A1 | 2/2003 | Foster et al. |
| 2003/0045907 A1 | 3/2003 | MacDonald |
| 2003/0053284 A1 | 3/2003 | Stevenson et al. |
| 2003/0055457 A1 | 3/2003 | MacDonald |
| 2003/0056820 A1 | 3/2003 | MacDonald |
| 2003/0074029 A1 | 4/2003 | Deno et al. |
| 2003/0081370 A1 | 5/2003 | Haskell et al. |
| 2003/0083570 A1 | 5/2003 | Cho et al. |
| 2003/0083723 A1 | 5/2003 | Wilkinson et al. |
| 2003/0083726 A1 | 5/2003 | Zeijlemaker et al. |
| 2003/0083728 A1 | 5/2003 | Greatbatch et al. |
| 2003/0100925 A1 | 5/2003 | Pape et al. |
| 2003/0109901 A1 | 6/2003 | Greatbatch |
| 2003/0111142 A1 | 6/2003 | Horton, Jr. et al. |
| 2003/0114897 A1 | 6/2003 | Von Arx et al. |
| 2003/0114898 A1 | 6/2003 | Von Arx et al. |
| 2003/0120197 A1 | 6/2003 | Kaneko et al. |
| 2003/0130647 A1 | 7/2003 | Gray et al. |
| 2003/0130700 A1 | 7/2003 | Miller et al. |
| 2003/0130701 A1 | 7/2003 | Miller |
| 2003/0130708 A1 | 7/2003 | Von Arx et al. |
| 2003/0135114 A1 | 7/2003 | Pacetti |
| 2003/0135160 A1 | 7/2003 | Gray et al. |
| 2003/0139096 A1 | 7/2003 | Stevenson et al. |
| 2003/0140931 A1 | 7/2003 | Zeijlemaker et al. |
| 2003/0144704 A1 | 7/2003 | Terry et al. |
| 2003/0144705 A1 | 7/2003 | Funke |
| 2003/0144706 A1 | 7/2003 | Funke |
| 2003/0144716 A1 | 7/2003 | Reinke et al. |
| 2003/0144717 A1 | 7/2003 | Hagele |
| 2003/0144718 A1 | 7/2003 | Zeijlemaker |
| 2003/0144719 A1 | 7/2003 | Zeijlemaker |
| 2003/0144720 A1 | 7/2003 | Villaseca et al. |
| 2003/0144721 A1 | 7/2003 | Villaseca et al. |
| 2003/0149459 A1 | 8/2003 | Von Arx et al. |
| 2003/0158584 A1 | 8/2003 | Cates et al. |
| 2003/0176900 A1 | 9/2003 | MacDonald |
| 2003/0179536 A1 | 9/2003 | Stevenson et al. |
| 2003/0191505 A1 | 10/2003 | Gryzwa et al. |
| 2003/0195570 A1 | 10/2003 | Deal et al. |
| 2003/0199755 A1 | 10/2003 | Halperin et al. |
| 2003/0204207 A1 | 10/2003 | MacDonald et al. |
| 2003/0204215 A1 | 10/2003 | Gunderson et al. |
| 2003/0204217 A1 * | 10/2003 | Greatbatch ............. 607/36 |
| 2003/0213604 A1 | 11/2003 | Stevenson et al. |
| 2003/0213605 A1 | 11/2003 | Brendel et al. |
| 2004/0005483 A1 | 1/2004 | Lin |
| 2004/0015162 A1 | 1/2004 | McGaffigan |
| 2004/0015197 A1 | 1/2004 | Gunderson |
| 2004/0019273 A1 | 1/2004 | Helfer et al. |
| 2004/0088012 A1 * | 5/2004 | Kroll et al. ............. 607/9 |
| 2004/0093432 A1 | 5/2004 | Luo et al. |
| 2005/0070975 A1 | 3/2005 | Zeijlemaker et al. |
| 2005/0113676 A1 | 5/2005 | Weiner et al. |
| 2005/0113873 A1 | 5/2005 | Weiner et al. |
| 2005/0113876 A1 | 5/2005 | Weiner et al. |
| 2005/0222656 A1 | 10/2005 | Wahlstrand et al. |
| 2005/0222657 A1 | 10/2005 | Wahlstrand et al. |
| 2005/0222658 A1 | 10/2005 | Hoegh et al. |
| 2005/0222659 A1 | 10/2005 | Olsen et al. |
| 2006/0025820 A1 | 2/2006 | Phillips et al. |
| 2006/0030774 A1 | 2/2006 | Gray et al. |
| 2006/0041294 A1 | 2/2006 | Gray |
| 2006/0167496 A1 | 7/2006 | Nelson et al. |
| 2006/0247747 A1 | 11/2006 | Olsen et al. |
| 2006/0247748 A1 | 11/2006 | Wahlstrand et al. |
| 2006/0271138 A1 | 11/2006 | MacDonald |
| 2006/0293591 A1 | 12/2006 | Wahlstrand et al. |
| 2007/0021814 A1 | 1/2007 | Inman et al. |
| 2007/0179577 A1 | 8/2007 | Marshall et al. |
| 2007/0179582 A1 | 8/2007 | Marshall et al. |
| 2007/0191914 A1 | 8/2007 | Stessman |
| 2007/0203523 A1 | 8/2007 | Betzold |
| 2007/0238975 A1 | 10/2007 | Zeijlemaker |
| 2008/0033497 A1 | 2/2008 | Bulkes et al. |
| 2008/0132985 A1 | 6/2008 | Wedan et al. |
| 2009/0138058 A1 | 5/2009 | Cooke et al. |
| 2009/0149906 A1 | 6/2009 | Ameri et al. |
| 2009/0204182 A1 | 8/2009 | Ameri |
| 2009/0210025 A1 | 8/2009 | Ameri |
| 2010/0087892 A1 | 4/2010 | Stubbs et al. |
| 2010/0211123 A1 | 8/2010 | Stubbs et al. |

FOREIGN PATENT DOCUMENTS

| | | |
|---|---|---|
| EP | 0591334 | 4/1994 |
| EP | 0705621 | 4/1996 |
| EP | 0719570 | 7/1996 |
| EP | 0836413 | 4/1998 |
| EP | 0331959 | 9/1998 |
| EP | 0870517 | 10/1998 |
| EP | 0891207 | 1/1999 |
| EP | 0891786 | 1/1999 |
| EP | 0980105 | 2/2000 |
| EP | 0989623 | 3/2000 |
| EP | 0989624 | 3/2000 |
| EP | 1007132 | 6/2000 |
| EP | 1007140 | 6/2000 |
| EP | 1060762 | 12/2000 |
| EP | 1061849 | 12/2000 |
| EP | 1109180 | 6/2001 |
| EP | 1128764 | 9/2001 |
| EP | 1191556 | 3/2002 |
| EP | 1271579 | 1/2003 |
| EP | 1308971 | 5/2003 |
| EP | 1372782 | 1/2004 |
| WO | WO 91/04069 | 4/1991 |
| WO | WO 96/38200 | 12/1996 |

| WO | WO 97/12645 | 4/1997 |
| WO | WO 00/54953 | 9/2000 |
| WO | WO 01/37286 | 5/2001 |
| WO | WO 01/80940 | 11/2001 |
| WO | WO 01/86774 | 11/2001 |
| WO | WO 02/056761 | 7/2002 |
| WO | WO 02/065895 | 8/2002 |
| WO | WO 02/072004 | 9/2002 |
| WO | WO 02/089665 | 11/2002 |
| WO | WO 02/092161 | 11/2002 |
| WO | WO 03/013199 | 2/2003 |
| WO | WO 03/037399 | 5/2003 |
| WO | WO 03/059445 | 7/2003 |
| WO | WO 03/061755 | 7/2003 |
| WO | WO 03/063946 | 8/2003 |
| WO | WO 03/063952 | 8/2003 |
| WO | WO 03/063954 | 8/2003 |
| WO | WO 03/063955 | 8/2003 |
| WO | WO 03/063956 | 8/2003 |
| WO | WO 03/063958 | 8/2003 |
| WO | WO 03/063962 | 8/2003 |
| WO | WO 03/070098 | 8/2003 |
| WO | WO 03/073449 | 9/2003 |
| WO | WO 03/073450 | 9/2003 |
| WO | WO 03/086538 | 10/2003 |
| WO | WO 03/090846 | 11/2003 |
| WO | WO 03/090854 | 11/2003 |
| WO | WO 03/095022 | 11/2003 |
| WO | WO 2006/124481 | 11/2006 |

OTHER PUBLICATIONS

Luechinger, Roger et al., "In vivo heating of pacemaker leads during magnetic resonance imaging", *European Heart Journal* 2005;26:376-383.

Shellock, Frank G. et al., "Cardiovascular catheters and accessories: ex vivo testing of ferromagnetism, heating, and artifacts associated with MRI", *Journal of Magnetic Resonance Imaging*, Nov./Dec. 1998; 8:1338-1342.

Shellock FG, "Reference manual for magnetic resonance safety, implants, and devices", pp. 136-139, 2008 ed. Los Angeles; Biomedical Research Publishing Group; 2008.

Kerr, Martha, Shock Rate Cut 70% With ICDs Programmed to First Deliver Antitachycardia Pacing: Results of the PainFREE Rx II Trial, Medscape CRM News, May 21, 2003.

Schueler et al., "MRI Compatibility and Visibility Assessment of Implantable Medical Devices", Journal of Magnetic Resonance Imaging, 9:596-603 (1999).

Sweeney, Michael O. et al., Appropriate and Inappropriate Ventricular Therapies, Quality of Life, and Mortality Among Primary and Secondary Prevention Implantable Cardioverter Defibrillator Patients: Results From the Pacing Fast VT REduces Shock ThErapies (PainFREE Rx II) Trial, American Heart Association, 2005.

Wilkoff, Bruce L. et al., "A Comparison of Empiric to Physician-Tailored Programming of Implantable Cardioverter-Defibrillators Results From the Prospective Randomized Multicenter EMPIRIC Trial," Journal of the American College of Cardiology, vol. 48, No. 2, 2006. doi:10.1016/j.jacc.2006.03.037.

* cited by examiner

SELECTIVELY CONNECTING THE TIP ELECTRODE DURING THERAPY FOR MRI SHIELDING

CROSS REFERENCE TO RELATED APPLICATION

The present application claims priority under 35 U.S.C. §119(e) to U.S. Provisional Patent Application No. 60/992,990 filed on Dec. 6, 2007, the entire contents of which are incorporated herein by reference.

TECHNICAL FIELD

Embodiments of the present invention relate to medical devices and the simultaneous delivery of diagnostic and therapeutic treatments. More specifically, embodiments of the present invention generally relate to implantable medical devices and minimizing the delivery of RF induced voltages to surrounding body tissue in an MRI environment.

BACKGROUND

Magnetic resonance imaging (MRI) is a non-invasive imaging method that utilizes nuclear magnetic resonance techniques to render images within a patient's body. Typically, MRI systems employ the use of a static magnetic coil having a magnetic field strength of between about 0.2 to 3 Teslas. During the procedure, the body tissue is briefly exposed to RF pulses of electromagnetic energy in a plane perpendicular to the magnetic field. The resultant electromagnetic energy from these pulses can be used to image the body tissue by measuring the relaxation properties of the excited atomic nuclei in the tissue.

During imaging, the electromagnetic radiation produced by the MRI system may be picked up by implantable device leads used in implantable medical devices such as pacemakers or cardiac defibrillators. This energy may be transferred through the lead to the electrode in contact with the tissue, which may lead to elevated temperatures at the point of contact. The degree of tissue heating is typically related to factors such as the length of the lead, the properties of the tissue near the lead, the conductivity or impedance of the lead, the shape of the lead, and the surface area of the lead electrodes. Exposure to a magnetic field may also induce an undesired voltage in the lead.

SUMMARY

Embodiments of the present invention generally relate to implantable medical devices and minimizing the delivery of RF induced voltages to surrounding body tissue in an MRI environment. An illustrative medical device includes a pulse generator configured to emit therapy pulses and a lead including an electrode configured to contact tissue in a body vessel. The lead includes a lead conductor electrically coupling the pulse generator with the electrode via a conductive path. The medical device further includes an electrode switch electrically connected between the lead conductor and the electrode. The electrode switch includes an open state preventing formation of the conductive path between the lead and the electrode. The electrode switch further includes a closed state allowing formation of the conductive path between the lead and the electrode upon reception of a voltage applied across the electrode switch which exceeds a threshold voltage. The electrode switch in the open state electrically shields the electrode from at least electromagnetic radiation within the body during an magnetic resonance imaging procedure, thereby preventing the inducement of a voltage on the electrode.

While some embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

Figure 1:
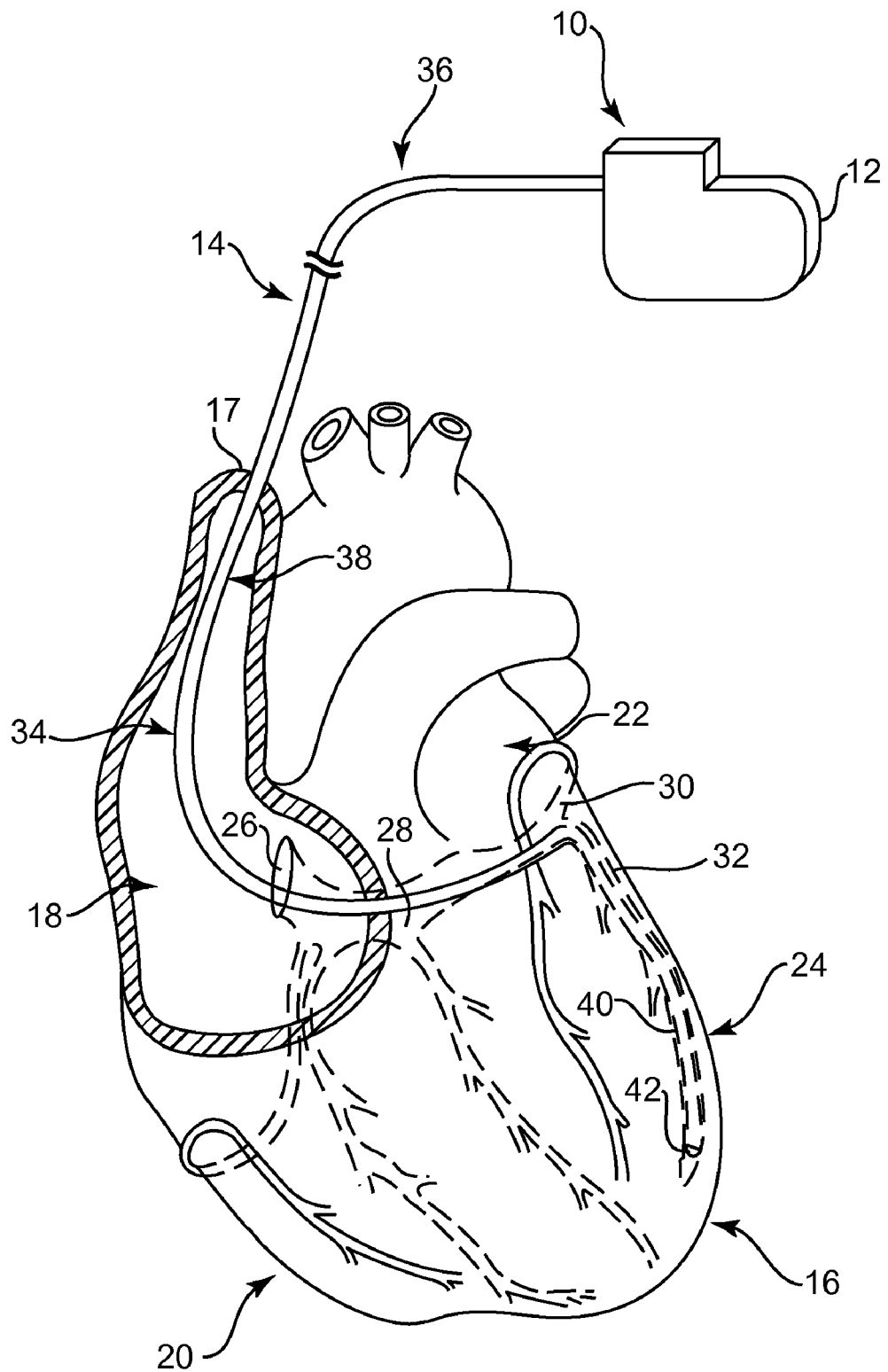
FIG. 1 is a schematic drawing of a cardiac rhythm management system including a pulse generator coupled to a lead deployed in a patient's heart.

While the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the present disclosure.

DETAILED DESCRIPTION

FIG. 1 is a schematic drawing of a cardiac rhythm management system 10 including a pulse generator 12 coupled to a lead 14 deployed in a patient's heart 16. According to some embodiments, the pulse generator 12 is typically implanted subcutaneously at an implantation location in the patient's chest or abdomen. As shown, the heart 16 includes, a superior vena cava 17, a right atrium 18 and a right ventricle 20, a left atrium 22 and a left ventricle 24, a coronary sinus ostium 26, a coronary sinus 28, and various cardiac branch vessels including a great cardiac vein 30 and an exemplary branch vessel 32.

As shown in FIG. 1, the lead 14 may include an elongated body 34 having a proximal region 36 and a distal region 38. The distal region 38 has a distal end 40 including an electrode 42, according to embodiments of the present invention. The lead 14 includes a lead conductor which electrically connects the pulse generator 12 to the electrode 42. To facilitate left ventricular pacing epicardially via an epicardial approach, lead 14 may be deployed in coronary veins 32 through the coronary sinus 28. In embodiments, the lead 14 can be implanted in other locations of the body such as the right ventricle, right atrium, or any other desired location in the body. Although FIG. 1 depicts the lead 14 as part of a cardiac rhythm management system 10 with an electrode 42, the lead 14 may alternatively include one or more sensors and/or one or more electrodes 42, and may couple the one or more sensors with a monitor in addition to, or in lieu of, the pulse generator 12. Additionally, although only one lead is illustrated in FIG. 1, the cardiac management system 10 may include any desired number of leads.

Figure 2:
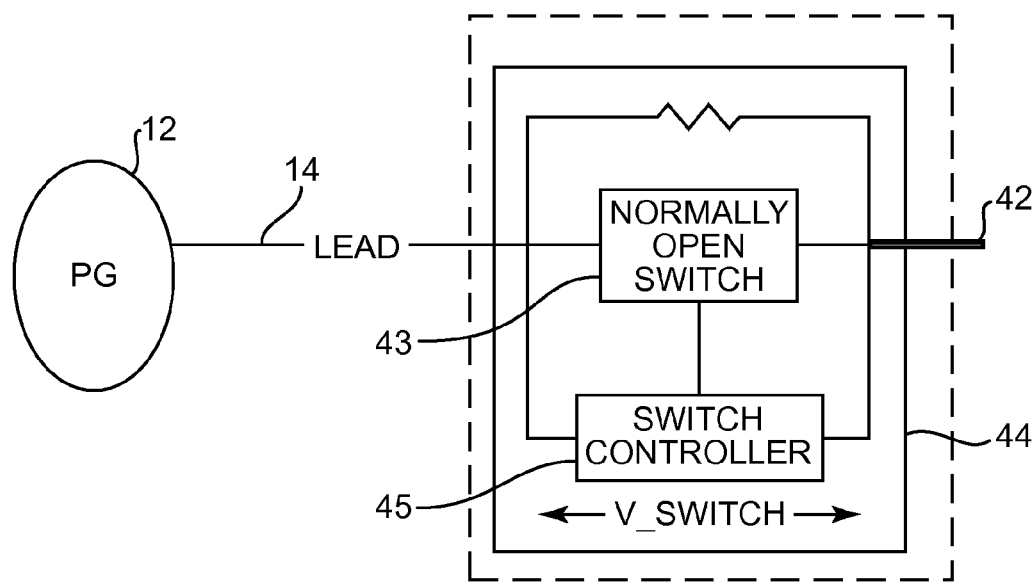
FIG. 2 illustrates a pulse generator and a lead with an electrode switch.

FIG. 2 illustrates a pulse generator 12 and a lead 14 with an electrode switch 44, according to some embodiments. In the embodiment of FIG. 2, the switch 44 is normally open, but is configured to close during the delivery of therapeutic pacing. In its normally open state, the switch 44 either creates an electrical discontinuity between the lead conductor and the electrode 42, or provides a relatively high resistance between the lead conductor and the electrode 42 and thus, between the lead conductor and the surrounding tissue. Accordingly, in its normally open state the switch 44 substantially shields the electrode 42 and surrounding tissue from receiving induced current pulses and/or electromagnetic radiation generated by an MRI system. Thus, in this configuration, the electrode 42 and surrounding tissue is isolated from the electromagnetic (e.g., RF) energy picked up by the lead 14 during magnetic resonance imaging. In embodiments, a relatively high resistance is a resistance high enough to substantially shield an electrode and surrounding tissue from receiving induced current pulses and/or electromagnetic radiation generated by an MRI system.

According to some embodiments, the switch 44 is configured to permit electrical continuity between the lead conductor and the electrode 42 when a voltage exceeding a threshold voltage is applied across the switch 44. Alternatively, in those embodiments in which the switch 44 increases the resistance between the lead conductor and the electrode 42 when open, the switch 44 can be configured to reduce its resistance when a voltage exceeding a threshold voltage is applied across the switch 44. In embodiments, this threshold voltage is selected as a result of the design of the switch 44 circuitry. Accordingly, the threshold voltage required to trigger the switch 44 may differ depending on the type and configuration of the switch 44. As an example, the threshold voltage of the switch 44 does not exceed a supply voltage such as 12V. As another example, the threshold voltage of a switch is fixed between 12V to 30V. As another example, the threshold voltage is variable.

In embodiments, the pulse generator 12 is configured to emit therapy pulses. Examples of therapy pulses include, but are not limited to, cardiac pacing pulses for heart failure and bradycardia; anti-tachy pacing and shock therapy for tachycardia; and pacing pulses for neurostimulation and pain mitigation. According to some embodiments, the pulse generator 12 is configured to provide a pacing pulse with a voltage amplitude higher than the threshold voltage of the switch 44, such that the switch 44 establishes a conductive path by completing the circuit between the lead conductor and the electrode 42 for the duration of the pacing pulse. In embodiments, the switch 44 includes a normally open switch 43 and a controller 45 that monitors the voltage applied across the normally open switch 43. In embodiments, when the voltage applied across the normally open switch 43 is greater than the threshold voltage, the controller 45 causes the switch 43 to close, creating a conductive path between the lead 14 and the electrode 42.

In embodiments, the threshold voltage of the switch 44 is selected such that the voltage level of the pacing pulse is sufficient to activate the switch, but the voltage level of energy in the lead induced by an MRI field by itself is not high enough to activate the switch 44. In this manner, the desired pacing pulses are effectively delivered to the electrode 42 and into the surrounding tissue while the undesirable MRI induced current and generated electromagnetic radiation are prevented from flowing through the switch 44 to the electrode 42.

Figure 3:
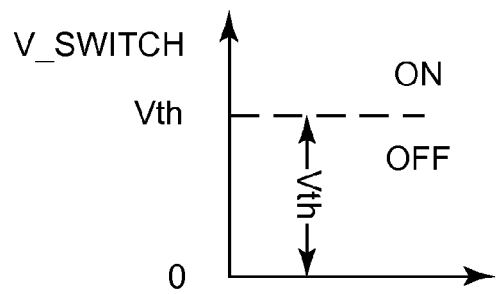
FIG. 3 graphically illustrates the state of the switch as "on" when the voltage applied across the switch is higher than the threshold voltage, and as "off" when the voltage applied across the switch is lower than or equal to the threshold voltage.
Figure 4:
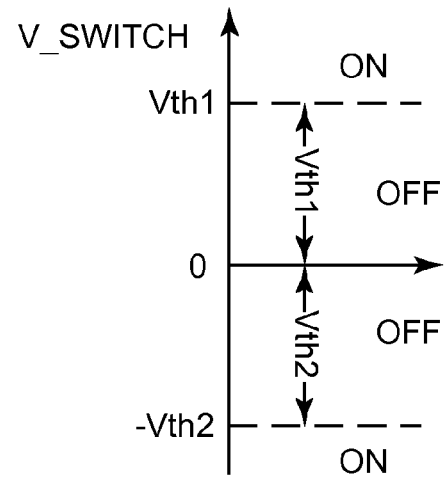
FIG. 4 graphically illustrates the state of the switch as "on" when the voltage applied across the switch is higher than Vth1 or lower than −Vth2, and as "off" when the voltage applied across the switch is between −Vth2 and Vth1.

FIG. 3 graphically illustrates the state of the switch 44 as "on" when the voltage applied across the switch 44 is higher than the threshold voltage, and as "off" when the voltage applied across the switch 44 is lower than or equal to the threshold voltage. In some embodiments, and as further illustrated in FIG. 4, the threshold voltage may be a negative or a positive voltage. For example, as illustrated in FIG. 4, the switch 44 is "on" when the voltage applied across the switch is higher than Vth1 or lower than −Vth2, and "off" when the voltage applied across the switch 44 is between −Vth2 and Vth1. In embodiments, Vth1 is equal to Vth2. In other embodiments, Vth1 is greater than or equal to Vth2.

Figure 5:
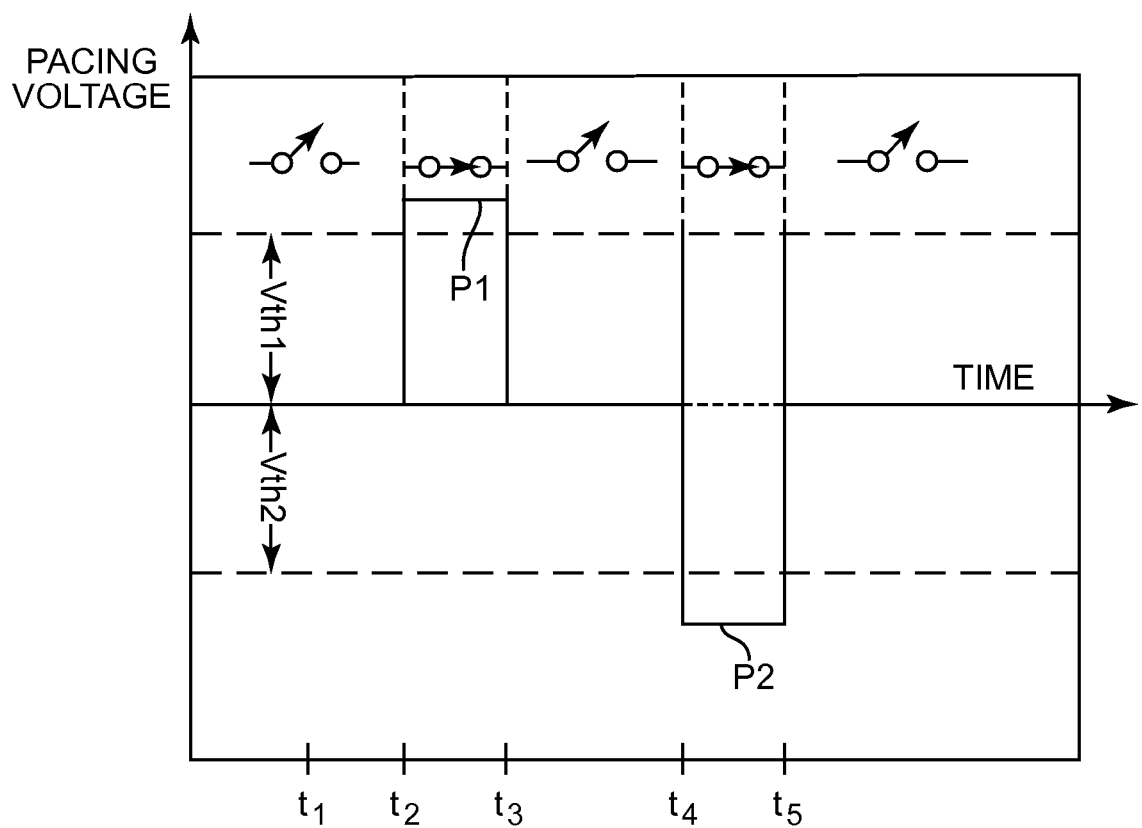
FIG. 5 illustrates the open or closed state of the switch versus time.

FIG. 5 illustrates the open or closed state of the switch 44 versus time, showing that the switch 44 is "closed" during the interval of the pacing pulse, and is "open" otherwise. At time $t_1$, the switch 44 is off (e.g., open) since the measured voltage across the switch 44 is zero. At time $t_2$, a first pacing pulse P1 is applied across the switch 44. Accordingly, the switch 44 is closed at time $t_2$. At time $t_3$, the switch 44 is open since the measured voltage across the switch 44 is zero. At time $t_4$, a second pacing pulse P2 with a negative voltage value is applied across the switch 44. Since the absolute value of the pacing pulse is greater than the absolute value of Vth2, the switch 44 is on. At time $t_5$, the switch 44 is off since the measured voltage across the switch 44 is zero.

In embodiments, the duration of pacing pulses and signals emitted from the pulse generator 12 are longer than a threshold duration, which means that the frequency of the pacing pulses is not higher than a threshold frequency (e.g., frequency=1/duration). In embodiments, the threshold duration is 60 nanoseconds and the threshold frequency is 8.5 MHz. In embodiments, any switch, controller, or device that receives pacing pulses or signals from the pulse generator 12 is responsive to pacing pulses or signals below a particular frequency. As an example, the switch 44 (FIG. 2) closes upon receiving one or more pacing pulses from the pulse generator 12 that are above the threshold voltage and have a duration longer than the threshold duration.

According to some embodiments, the switch 44 is an electrical switch such as, for example, a diode for alternating current ("DIAC") switch, which changes its resistance based upon the magnitude of the applied voltage. According to other embodiments, the switch 44 is a mechanical switch, with additional circuitry to monitor the voltage applied across the switch 44 and to accomplish closure of the switch 44 when the voltage applied across the switch exceeds a predetermined voltage level. In some embodiment, the switch 44 may be a DIAC, TRISIL™, or similar device. The switch 44 may include other types of circuit components, including, but not limited to transistors, diodes, field-effect transistors ("FET"), and/or electro-mechanical relays. According to some embodiments the switch 44 may be unipolar or bipolar, depending on the application.

Figure 6:
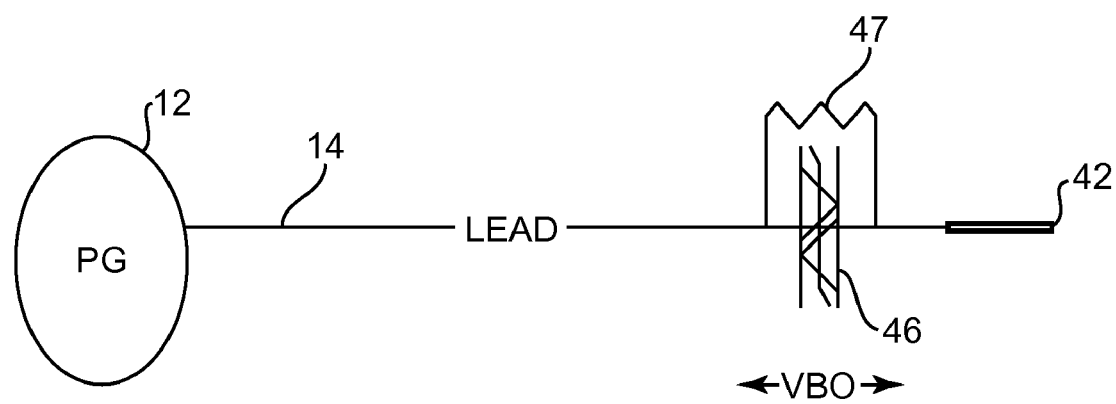
FIG. 6 illustrates a pulse generator and a lead with a switch between the lead conductor and the electrode.

FIG. 6 illustrates a pulse generator 12 and a lead 14 with a DIAC, TRISIL™, or similar device 46 between the lead conductor and the electrode 42. In some embodiments, the device 46 is constructed with discreet components, and exhibits a large resistance (approaching that of an open circuit) until a voltage which is higher than a threshold voltage of the device 46 is applied across the device 46, which then causes the resistance of the device 46 to drop significantly (approaching that of a short circuit to establish a conductive path). In embodiments, a high impedance resistor 47 is connected in parallel with the switch 46. As an example, the impedance of the resistor 47 is high enough to prevent electromagnetic energy picked up by the lead 14 from transferring to the surrounding tissue via the electrode 42. However, the impedance of the resistor 47 is low enough to provide a conductive path between the pulse generator 12 and a common ground to permit sensing of applications and re-charging of capacitors located in the pulse generator 12, which might otherwise be inhibited by including the normally-open switch at the electrode 42.

Figure 7:
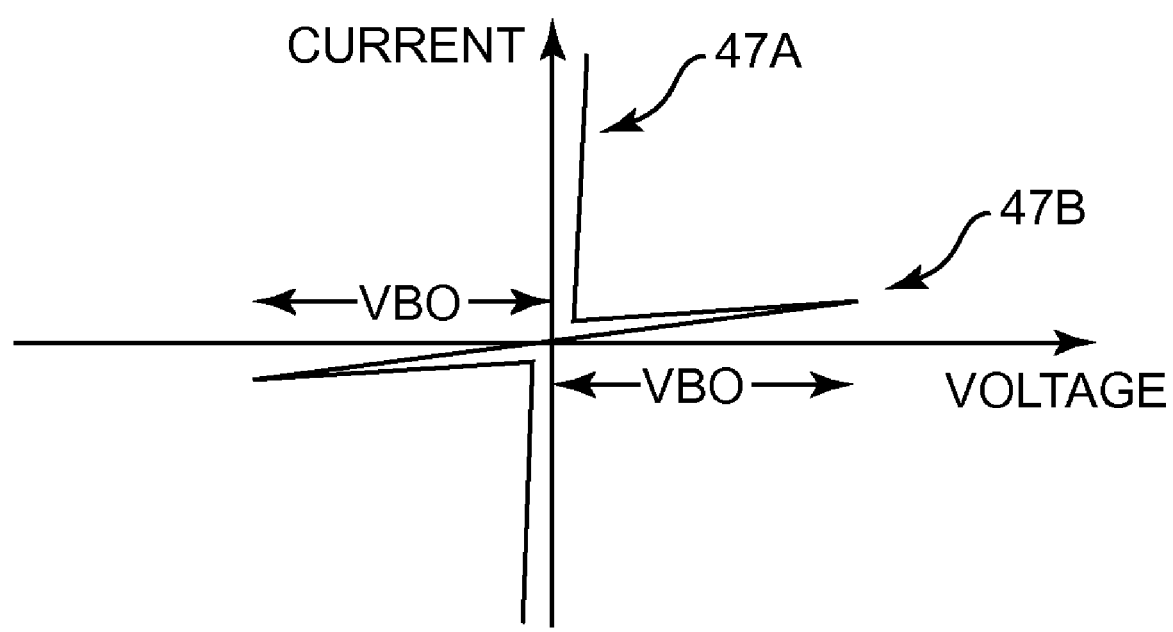
FIG. 7 illustrates a characteristic voltage-current curve for the switch illustrated in FIGS. 6 and 8.

FIG. 7 illustrates a characteristic voltage-current curve for the device 46 of FIG. 6 according to some embodiments. As illustrated in FIG. 7, the magnitude of the voltage across the device 46 increases at a low current until the threshold voltage (shown as "VBO") is exceeded. When the threshold voltage is exceeded, the device 46 switches to a conductive state, at which point the resistance breaks down and current flows easily across the device 46 as indicated at 47A in FIG. 7. The device 46 switches back to a non-conductive state when the current flowing through the device 46 falls below a specified level, at which point the high resistance of the device is re-established as indicated at 47B in FIG. 7.

Figure 8:
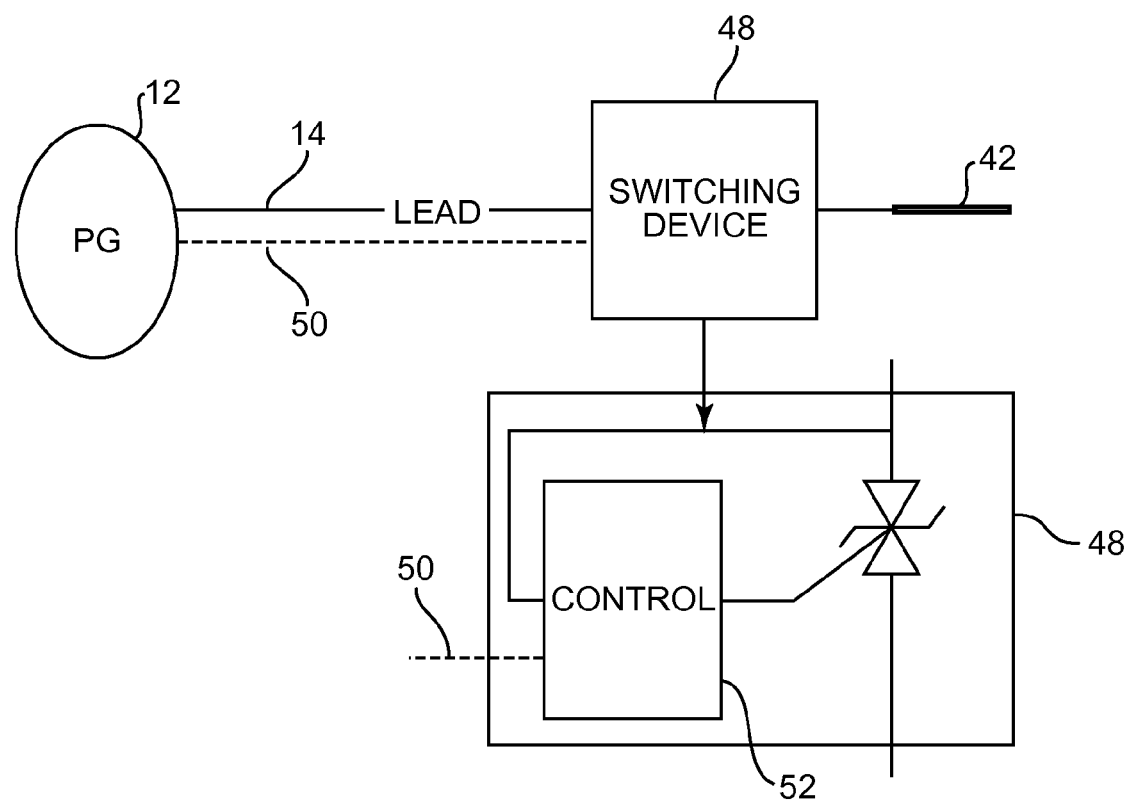
FIG. 8 illustrates a pulse generator and a lead with a switch between the lead conductor and the electrode along with an optional control line for varying the threshold voltage of the device or giving a direct command to turn the switch on or off.

FIG. 8 illustrates a pulse generator 12 and a lead 14 with a switching device 48 between the lead conductor and the electrode 42. An expanded view of the switching device 48 is provided below the arrow. In embodiments, the switching device 48 includes an optional control line 50 for varying the threshold voltage of the switching device 48. According to some embodiments, a controller 52 integrated within the switching device 48 receives a control signal from the pulse generator 12 via the control line 50, and changes the threshold voltage across the switching device 48 based on the control signal. In certain embodiments, the controller 52 selects between two or more circuits having characteristic voltage-current curves similar to that of FIG. 7 but with different threshold voltages. In other embodiments, the pulse generator 12 directly commands the controller 52 via control line 50 to turn the device on or off.

During an MRI scan, the switching device 48 can be used alone to isolate the electrode 42 from the rest of the conductor within the lead 14. Therapy applied voltages which exceed the breakdown voltage of the switching device 48 create a low impedance path for the duration of the pulse. After the pulse is removed, the switching device 48 resumes a high impedance state and opens the electrical connection between the lead conductor and the electrode 42. As depicted in FIG. 8, a separate control line 50 can be used to control the gate of the switching device 48 or change its threshold voltage. According to some embodiments, using a DIAC, TRISIL™, or similar device can be ideal for use in a defibrillator or other device that applies high voltages to an electrode. Typical DIACs with a threshold voltage of 20 to 30 volts may be sufficient for use in a defibrillator, for example. In some embodiments, a special version of a DIAC constructed with discrete components such as silicon-controlled rectifiers ("SCR")/triodes for alternating current ("TRIAC") and controlling (gate firing) circuits may be used for therapy voltages lower than 20 to 30 volts.

The controller 52 may be directly controlled through the main lead 14 or through a separate line 50. In embodiments, the controller 52 is any desired microcontroller. The controller 52 may also be programmed dynamically via any external device such as a remote terminal, according to embodiments. As an example, a remote terminal communicates with the pulse generator 12 via any suitable wireless interface. Accordingly, in this example, commands from the remote device are forwarded from the pulse generator 12 to the controller 52 via the control line 50.

Figure 9:
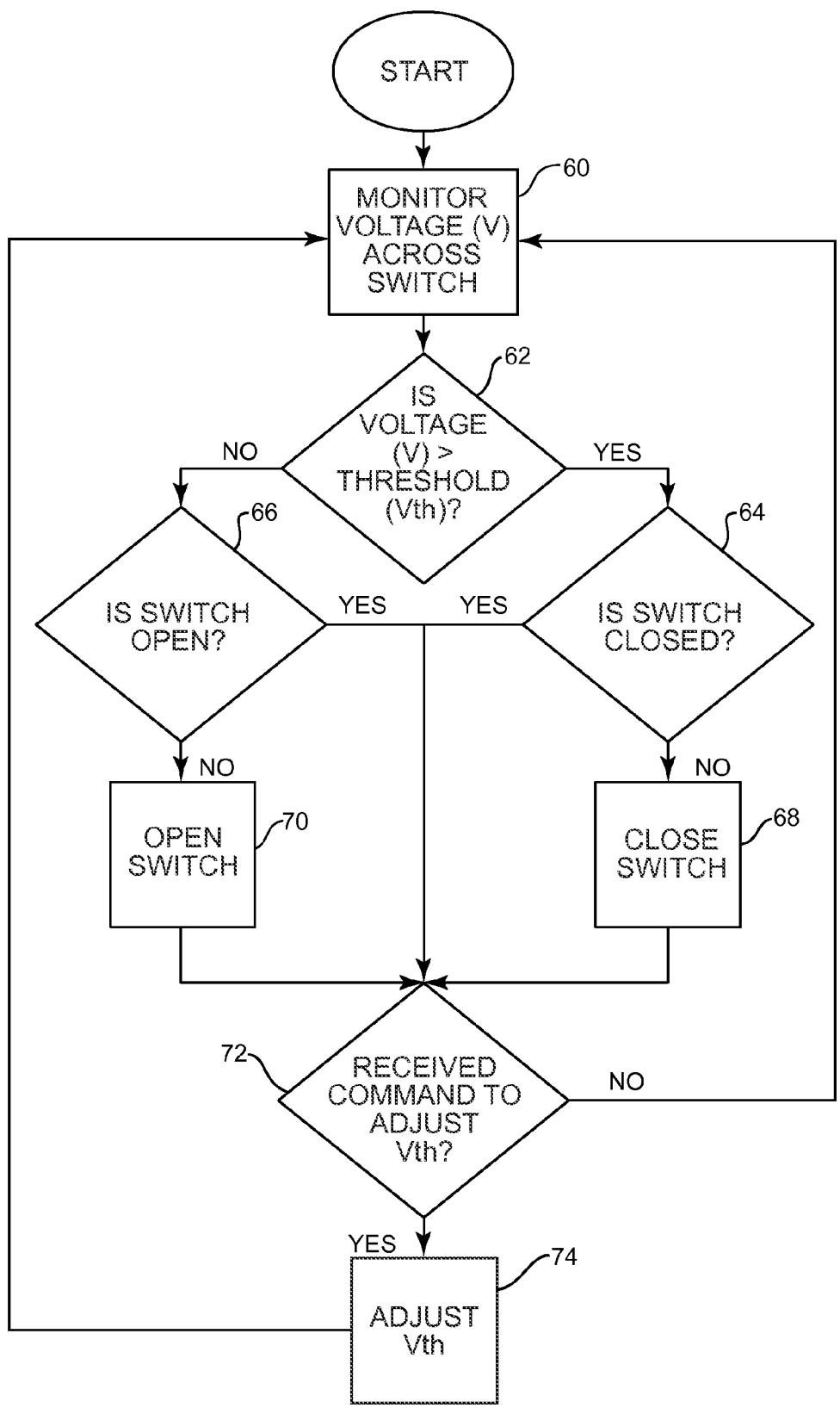
FIG. 9 illustrates an example method for monitoring a voltage across a switch and adjusting a voltage threshold.

FIG. 9 illustrates an example process for monitoring a voltage across at a switch and adjusting a voltage threshold using the switching device 48 of FIG. 8. The process may generally begin at block 60 where the switch controller 52 monitors a voltage (V) across the switching device 48. In embodiments, the voltage (V) is provided by the pulse generator 12. After measuring the voltage (V), the switch controller 52 determines if the measured voltage (V) is greater than the voltage threshold (Vth) 62. If V>Vth, the switch controller 52 determines if the switching device 48 is closed at block 64. If the switch controller 52 determines that the switching device 48 is not closed, the switch controller 52 closes the switching device (block 68). If the switch controller 52 determines that the switching device 48 is closed at block 64, the switch controller 52 proceeds to determine if a command to adjust Vth has been received at block at block 72. If V≦Vth (block 62), the switch controller 52 determines if the switch 48 is open at block 66. If the switching device 48 is not open, the switch controller 52 opens the switching device 48 (block 70). If switching device 48 is open, the switch controller proceeds to determine if a command to adjust Vth has been received at block 72.

If the switch controller 52 determines that a command to adjust Vth has not been received (block 72), the switch controller 52 returns to monitoring the voltage (V) across the switching device 48 (block 60). If the switch controller 52 determines that a command to adjust Vth has been received, the switch controller 52 adjusts Vth 72 based on the command. In some embodiments, the switch controller 52 receives the command from the pulse generator 12 via the control line 50.

In embodiments, the command is a voltage "high" or a voltage "low." Upon receiving the voltage "high" (e.g., 1) or voltage "low" (e.g., 0) from the pulse generator 12, the switch controller 52 switches between a first voltage threshold and a second voltage threshold. In embodiments, when the switching device 48 includes more than two voltage thresholds, the switch controller 52 receives a series of commands from the pulse generator 12. For example, a switching device 48 with four voltage thresholds (e.g., Vth1, Vth2, Vth3, and Vth4) receives two signals from the pulse generator 12 via the control line 50 before switching voltage thresholds. As an example, the four threshold voltages may be distinguished by the following control signals: Vth1=00, Vth2=01, Vth3=10, Vth4=11. Accordingly, when the switch controller 52 receives two voltage "low" signals in series (e.g., 00), the switch controller 52 switches to Vth1. Similarly, when the switch controller 52 receives a voltage "high" and a voltage "low" in series (e.g., 01), the switch controller 52 switches to Vth2. In embodiments, the switching device 48 is not limited to any particular number of voltage thresholds, and the switch controller 52 is configured to handle any signaling pattern transmitted from the pulse generator 12.

Figure 10:
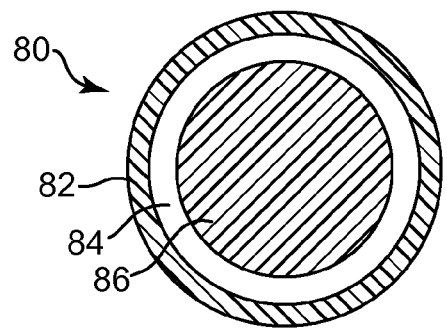
FIG. 10 is a cross-sectional view of an illustrative lead.

FIG. 10 illustrates a cross-sectional view of a lead 80, according to embodiments of the present invention. As shown in FIG. 10, lead 80 includes an outer conductor 82, an insulating layer of material 84 with a breakdown voltage of a certain threshold, and an inner conductor 86. According to some embodiments, a pulse generator 12 is in electrical communication with the outer conductor 82, and the electrode 42 is in electrical communication with the inner conductor 86. In embodiments, the insulating layer of material 84 is a varistor (e.g., variable resistor). Example varistors are disclosed in U.S. patent application Ser. No. 11/498,916 entitled "Transient Voltage Protection Circuit Boards and Manufacturing Methods," the entire contents of which are incorporated herein by reference. In other embodiments, the insulating layer of material 84 is any other desired material having a breakdown voltage of a certain threshold.

Electromagnetic radiation generated by or current induced by an MRI system is received by the outer conductor 82, but is not transmitted through the insulating layer 84, which acts as a highly resistive barrier until the threshold voltage is exceeded. The pulse generator 12 may then generate a pulse with a voltage value exceeding the threshold voltage of the insulating layer 84, at which point the breakdown voltage of the insulating layer 84 is exceeded and the pacing pulse proceeds through the insulating layer 84, into the inner conductor 86, and to the electrode 42 and surrounding tissue. The lead 80 cross section as depicted in FIG. 10 may be formed along the length of a lead, or may optionally be formed only along the distal section of the lead so as to minimize induced currents on the inner conductor 86 at or near the electrode 42 during an MRI scan. In one alternative embodiment, the pulse generator 12 is in electrical communication with the inner conductor 86, and the electrode 42 is in electrical communication with the outer conductor 82.

Figure 11:
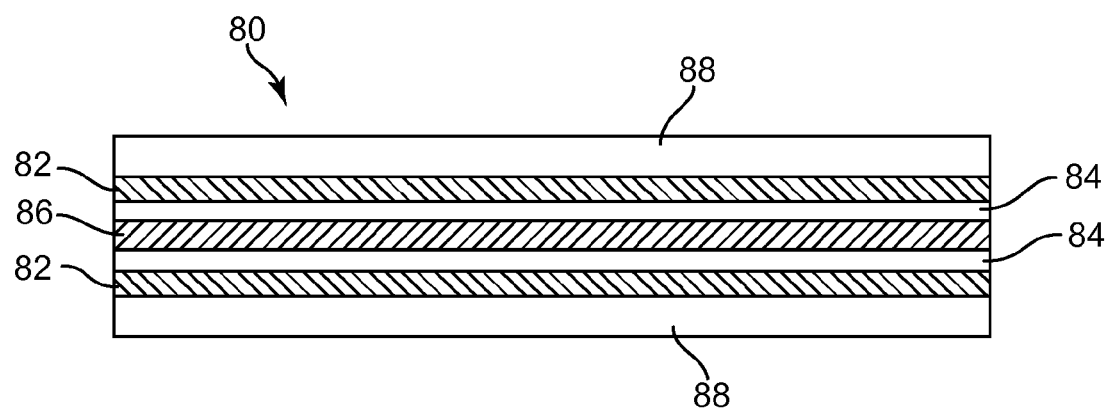
FIG. 11 is another cross-sectional view of the lead.

FIG. 11 illustrates a longitudinal cross-sectional view of the lead 80 according to some embodiments of the present invention. In some embodiments, the lead 80 includes an outer insulating layer 88 encapsulating the outer conductor 82. As illustrated in FIG. 11, the insulating material 84 is positioned between the outer conductor 82 and the inner conductor 86. In embodiments, the pulse generator 12 connects to the outer conductor 82 on a proximal portion of the lead 80, and the electrode 42 connects to the inner conductor 86 on a distal portion of the lead 80. In other embodiments, the pulse generator 12 connects to the inner conductor 86 on the distal portion of the lead 80, and the electrode 42 connects to the outer conductor 82 on the proximal portion of the lead 80.

Various modifications and additions can be made to the exemplary embodiments discussed without departing from the scope of the present invention. For example, while the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the present disclosure, together with all equivalents thereof.

What is claimed is:

1. A medical device, comprising:
    a pulse generator configured to emit one or more therapy pulses;
    a lead including an electrode configured to contact body tissue in a body vessel and a lead conductor connecting the pulse generator with the electrode via a conductive path;
    an electrode switch electrically coupled between the lead conductor and the electrode, the electrode switch including an open state preventing the conductive path between the lead conductor and the electrode, the electrode switch including a closed state allowing formation of the conductive path between the lead conductor and the electrode upon reception of a voltage applied across the electrode switch which exceeds a threshold voltage, wherein the electrode switch comprises a threshold controller and a control line connecting the threshold controller to the pulse generator, and wherein the threshold controller is configured to receive at least one signal from the pulse generator to adjust the threshold voltage to another threshold voltage; and
    wherein the electrode switch in the open state is configured to electrically shield the electrode from at least electromagnetic radiation and induced voltages during magnetic resonance imaging.

2. The medical device according to claim 1, wherein the electrode switch further comprises:
    a normally open switch configured to receive the one or more therapy pulses from the pulse generator, the normally open switch including the open state and the closed state, and
    a switch controller configured to monitor a voltage applied across the normally open switch, the switch controller configured to switch the normally open switch from the open state to the closed state upon a voltage applied across the normally open switch exceeding the threshold voltage.

3. The medical device of claim 1, wherein the electrode switch is a diode for alternating current (DIAC) device.

4. The medical device of claim 1, wherein the voltage applied across the electrode switch is from at least one therapy pulse from the one or more therapy pulses emitted from the pulse generator.

5. The medical device of claim 4, wherein the voltage applied across the electrode from the at least one therapy pulse exceeds the threshold voltage.

6. The medical device of claim 1, further comprising:
    a high impedance resistor electrically connected in parallel with the electrode switch, the high impedance resistor configured to shield the electrode from electromagnetic radiation and induced voltages during magnetic resonance imaging and to provide another conductive path between the pulse generator and electrode when the electrode switch is in the open state.

7. The medical device of claim 1, wherein
    the pulse generator is further configured to emit the one or more therapy pulses at a duration equal to or greater than a threshold duration, and
    the electrode switch is further configured to operate in the closed state upon reception of the one or more therapy pulses having a voltage level exceeding the threshold voltage and a duration exceeding the threshold duration.

8. A method for monitoring a voltage applied across a switch, said method comprising:
    monitoring a voltage across an electrode switch electrically coupled between a lead and an electrode, the electrode configured to contact tissue in a body vessel, the lead connecting a pulse generator with the electrode via a conductive path, the electrode switch including a threshold controller and a control line connecting the threshold controller to the pulse generator;
    providing at least one signal from the pulse generator to the threshold controller to set a threshold voltage of the electrode switch;

switching the electrode switch to an open state when the monitored voltage across the electrode switch is at or below the voltage threshold, the open state of the electrode switch preventing formation of the conductive path between the lead and the electrode;

switching the electrode switch to a closed state when the monitored voltage across the electrode switch exceeds the voltage threshold, the closed state of the electrode switch allowing formation of the conductive path between the lead and the electrode; and wherein the electrode switch in the open state is configured to electrically shield the electrode from at least electromagnetic radiation and induced voltages during magnetic resonance imaging.

9. The method of claim 8, further comprising:

receiving one or more therapy pulses from the pulse generator, wherein the voltage applied across the electrode switch is the one or more therapy pulses.

10. The method of claim 9, wherein the one or more therapy pulses exceeds the threshold voltage.

11. The method of claim 9, further comprising:

receiving the one or more therapy pulses from the pulse generator, the one or more therapy pulses having a duration greater than a threshold duration; and switching the electrode switch to the closed state upon reception of the one or more therapy pulses having a voltage level exceeding the threshold voltage and a duration exceeding the threshold duration.

12. The method according to claim 8, further comprising:

establishing another conductive path between the lead conductor and electrode via a high impedance resistor electrically connected in parallel with the electrode switch, the high impedance resistor configured to shield the electrode from electromagnetic radiation and induced voltages during magnetic resonance imaging.

13. The method of claim 8, wherein the electrode switch is a diode for alternating current (DIAC) device.

\* \* \* \* \*